United States Patent
Ichikawa et al.

(10) Patent No.: US 8,668,680 B2
(45) Date of Patent: Mar. 11, 2014

(54) DISPOSABLE WEARING ARTICLE

(75) Inventors: Makoto Ichikawa, Kanonji (JP);
Kenichi Sasayama, Kanonji (JP);
Hiroki Yamamoto, Kanonji (JP); Kazuo Ukegawa, Kanonji (JP); Akihide Ninomiya, Kanonji (JP)

(73) Assignee: Unicharm Corporation, Ehime (JP)

( * ) Notice: Subject to any disclaimer, the term of this patent is extended or adjusted under 35 U.S.C. 154(b) by 0 days.

(21) Appl. No.: 13/515,839

(22) PCT Filed: Dec. 16, 2010

(86) PCT No.: PCT/JP2010/072714
§ 371 (c)(1),
(2), (4) Date: Jun. 14, 2012

(87) PCT Pub. No.: WO2011/081034
PCT Pub. Date: Jul. 7, 2011

(65) Prior Publication Data
US 2012/0259304 A1    Oct. 11, 2012

(30) Foreign Application Priority Data

Dec. 28, 2009  (JP) .................................. 2009-298929

(51) Int. Cl.
*A61F 13/20* (2006.01)
*A61F 13/15* (2006.01)

(52) U.S. Cl.
USPC .............. 604/385.3; 604/385.03; 604/385.13; 604/385.23; 604/385.24; 604/385.25; 604/385.27; 604/385.29

(58) Field of Classification Search
USPC ............... 604/385.3, 385.03, 385.13, 385.23, 604/385.24, 385.25, 385.27, 385.29
See application file for complete search history.

(56) References Cited

U.S. PATENT DOCUMENTS

| | | | |
|---|---|---|---|
| 6,717,028 B1* | 4/2004 | Oberstadt | 604/365 |
| 2005/0038404 A1* | 2/2005 | Takino et al. | 604/385.27 |
| 2005/0234421 A1* | 10/2005 | Mishima et al. | 604/385.01 |

FOREIGN PATENT DOCUMENTS

| | | |
|---|---|---|
| JP | 432718 | 3/1992 |
| JP | 2008212249 | 9/2008 |
| JP | 2009207778 | 9/2009 |

OTHER PUBLICATIONS

International Search Report for PCT/JP2010/072714 mailed Mar. 15, 2011.

* cited by examiner

*Primary Examiner* — Tatyana Zalukaeva
*Assistant Examiner* — Andrew J Mensh
(74) *Attorney, Agent, or Firm* — Lowe Hauptman & Ham, LLP

(57) ABSTRACT

A disposable wearing article includes a liquid-absorbent structure that is adapted to be spaced from the wearer's skin to protect the wearer's skin from being soiled with body waste. A crotch member defining parts of front and rear waist regions and a crotch region has a front end lying in the front waist region and a rear end lying in the rear waist region wherein at least one of the front and rear ends defines non-bonded regions in an intermediate zone as viewed in the transverse direction X of the crotch member and is attached to the outer surface of an elastic waist panel by the intermediary of square U-shaped bonded regions opening toward the crotch region. In areas defining the non-bonded regions, body waste retaining space(s) are formed between the elastic waist panel and the crotch member.

9 Claims, 6 Drawing Sheets

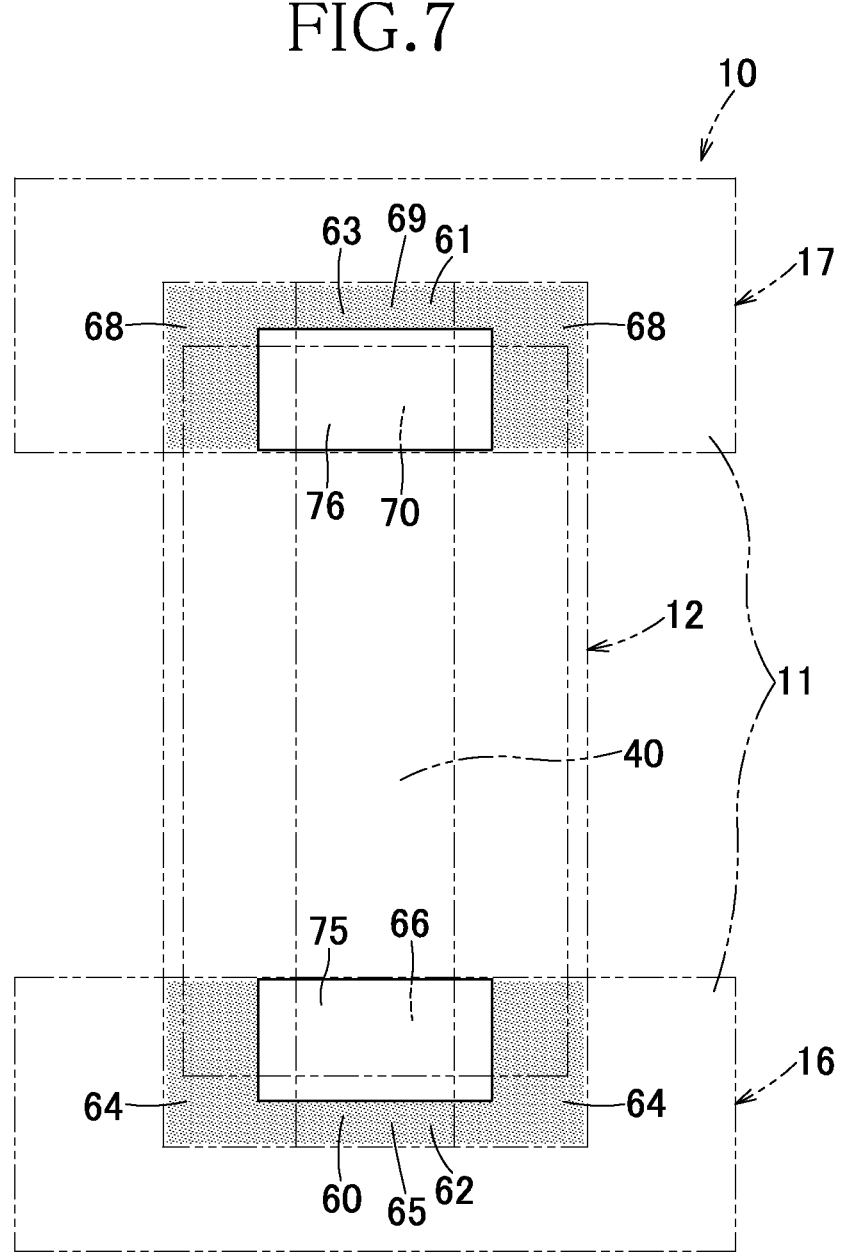

DISPOSABLE WEARING ARTICLE

RELATED APPLICATIONS

The present application is a national phase of PCT/JP2010/072714 filed Dec. 16, 2010 and is based on, and claims priority from, Japanese Application Number 2009-298929, filed Dec. 28, 2009.

TECHNICAL FIELD

The present invention relates to disposable wearing articles and more particularly to disposable wearing articles such as disposable diapers, disposable toilet-training pants, disposable incontinent pants, disposable sanitary pants and the like, each formed in front and rear waist regions with spaces adapted for temporary retention of body waste.

BACKGROUND

Conventionally, wearing articles each formed of an annular elastic waist panel and a crotch member defining a crotch region are known. For example, PTL 1 discloses a wearing article including an annular elastic waist panel and a crotch member inclusive of a liquid-absorbent structure wherein the crotch member is attached to the inner surface of the elastic waist panel.

CITATION LIST

Patent Literature

{PTL 1} JP 2008-212249 A

SUMMARY OF INVENTION

Technical Problem

In the wearing article disclosed by PTL 1, the crotch member is attached to the inner surface of the elastic waist panel and, in consequence, body waste excreted onto the liquid-absorbent structure should become adherent to the wearer's skin, making the wearer uncomfortable, and cause skin troubles such as skin irritation. In addition, body waste having flowed into the front and rear waist regions might leak out from these regions.

An object of the present invention is to improve the known wearing article and to provide a wearing article improved so that, with the wearing article put on the wearer's body, the wearer's skin may be spaced apart from a liquid-absorbent structure so as not to be soiled with body waste and the body waste having flowed into the front and rear waist regions may be prevented from leaking out beyond these waist regions by providing the front and rear waist regions with body waste retaining spaces.

Solution to Problem

According to the present invention, there is provided a disposable wearing article having a longitudinal direction and a transverse direction orthogonal thereto, including a front waist region, a rear waist region, a crotch region extending between the front and rear waist region, an annular elastic waist panel defining the front and rear waist regions, and a crotch member attached to the elastic waist panel so as to define parts of the front and rear waist regions and the crotch region.

The features of the present invention resides in that the crotch member has a front end lying in the front waist region and a rear end lying in the rear waist region; at least one of the front and rear ends defines a non-bonded region in an intermediate zone as viewed in the transverse direction of the crotch member and is attached to the outer surface of the elastic waist panel by the intermediary of a square U-shaped bonded region opening toward the crotch region; and, in an area defining the non-bonded region, a body waste retaining space is formed between the elastic waist panel and the crotch member.

The present invention further includes embodiments as follows:

(1) The crotch member includes a pair of lateral elastic regions extending in the longitudinal direction on opposite sides of the crotch region, a liquid-absorbent structure extending in the longitudinal direction is provided on the inner surface of the crotch region, and the non-bonded region is defined in an area occupied by the liquid-absorbent structure between the pair of lateral elastic regions.

(2) Leakage-barrier sheets made of a liquid-impervious but moisture-pervious plastic sheet or a fibrous nonwoven fabric sheet are attached to the elastic waist panel in the regions corresponding to the non-bonded regions.

Advantageous Effects of Invention

According to the present invention, the non-bonded region is defined in at least one of the front and rear waist regions and the body waste retaining space(s) may be formed between the elastic waist panel and the crotch member. Such a unique arrangement ensures to prevent body waste having leached or flowed into these waist regions from leaking out of the wearing article.

BRIEF DESCRIPTION OF DRAWINGS

FIG. 7 is a developed plan view similar to FIG. 6, showing a second embodiment of the present invention.

DESCRIPTION OF EMBODIMENTS

First Embodiment

Figure 1:
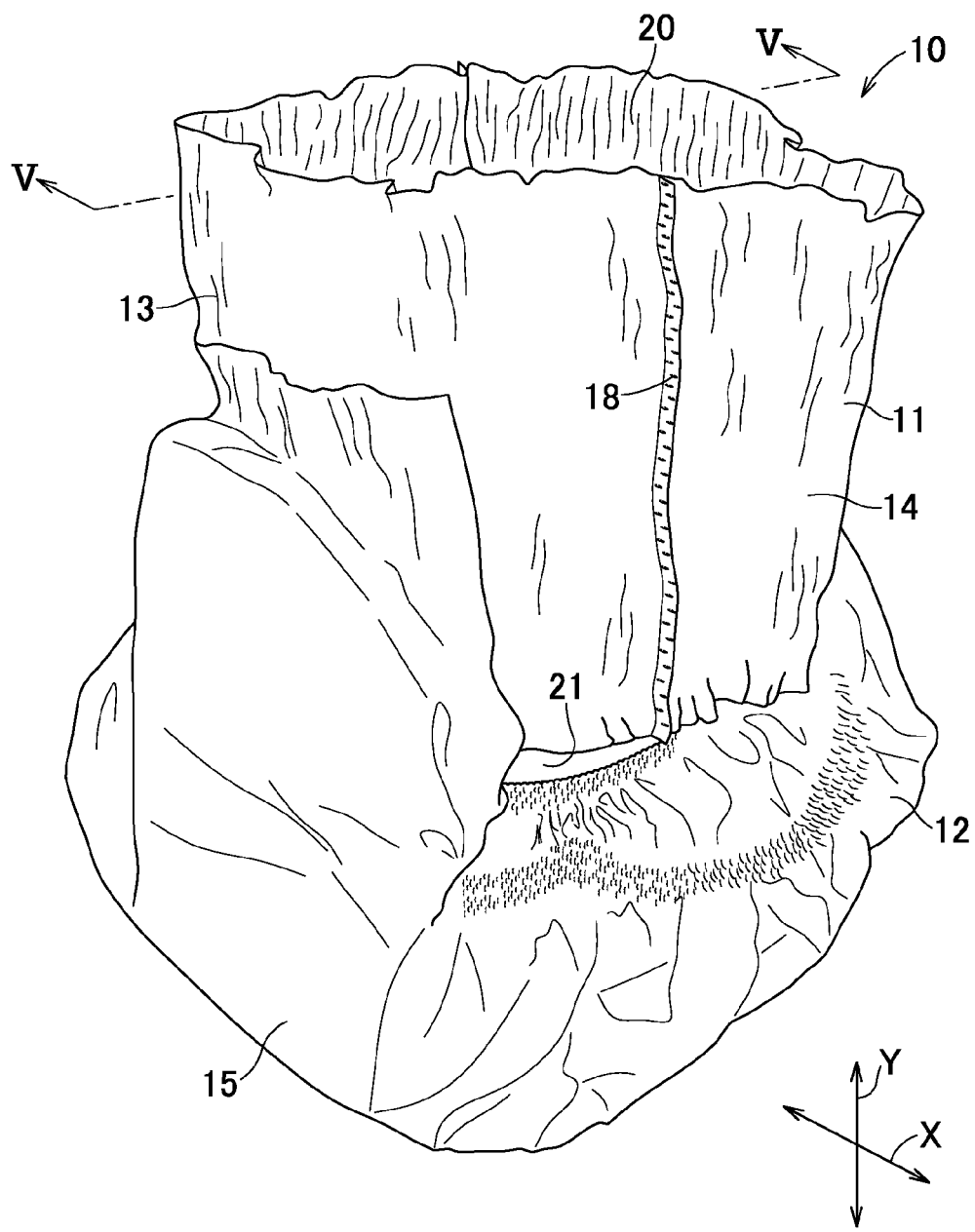
FIG. 1 is a perspective view of a disposable diaper as one example of disposable wearing articles according to a first embodiment of the present invention.
Figure 2:
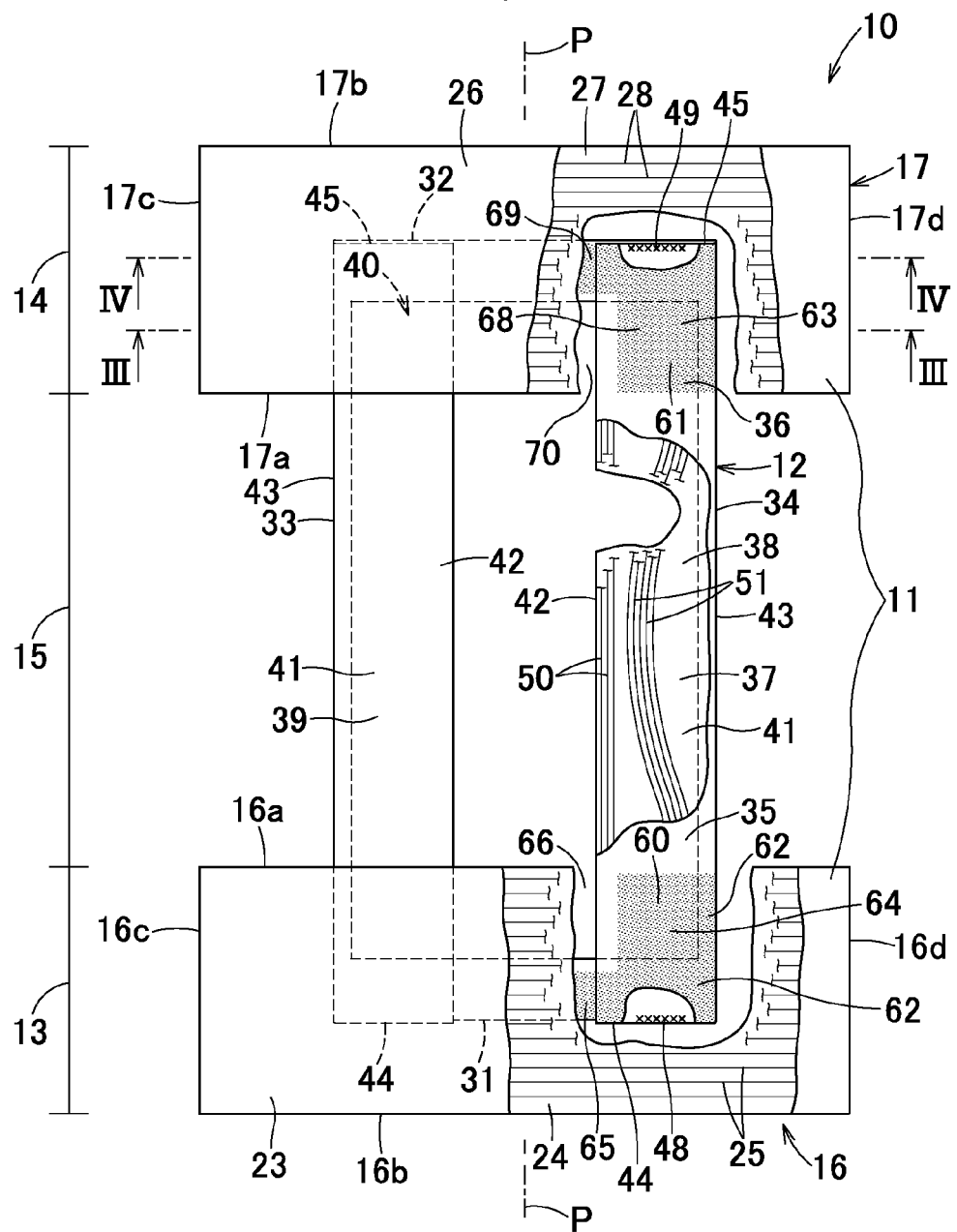
FIG. 2 is a partially cutaway developed plan view of the diaper having front and rear waist regions peeled off from each other along side seams and developed in a front-back direction as viewed from the inner side of the diaper.
Figure 3:
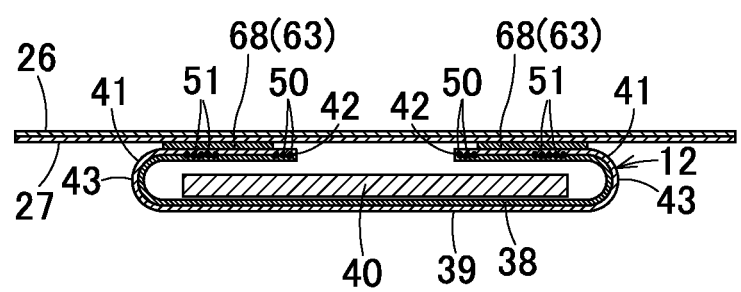
FIG. 3 is a sectional view taken along line in FIG. 2.
Figure 4:
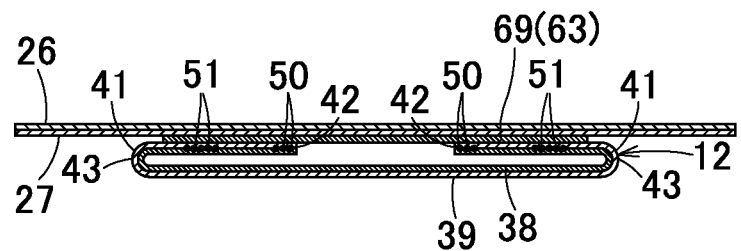
FIG. 4 is a sectional view taken along line IV-IV in FIG. 2.
Figure 5:
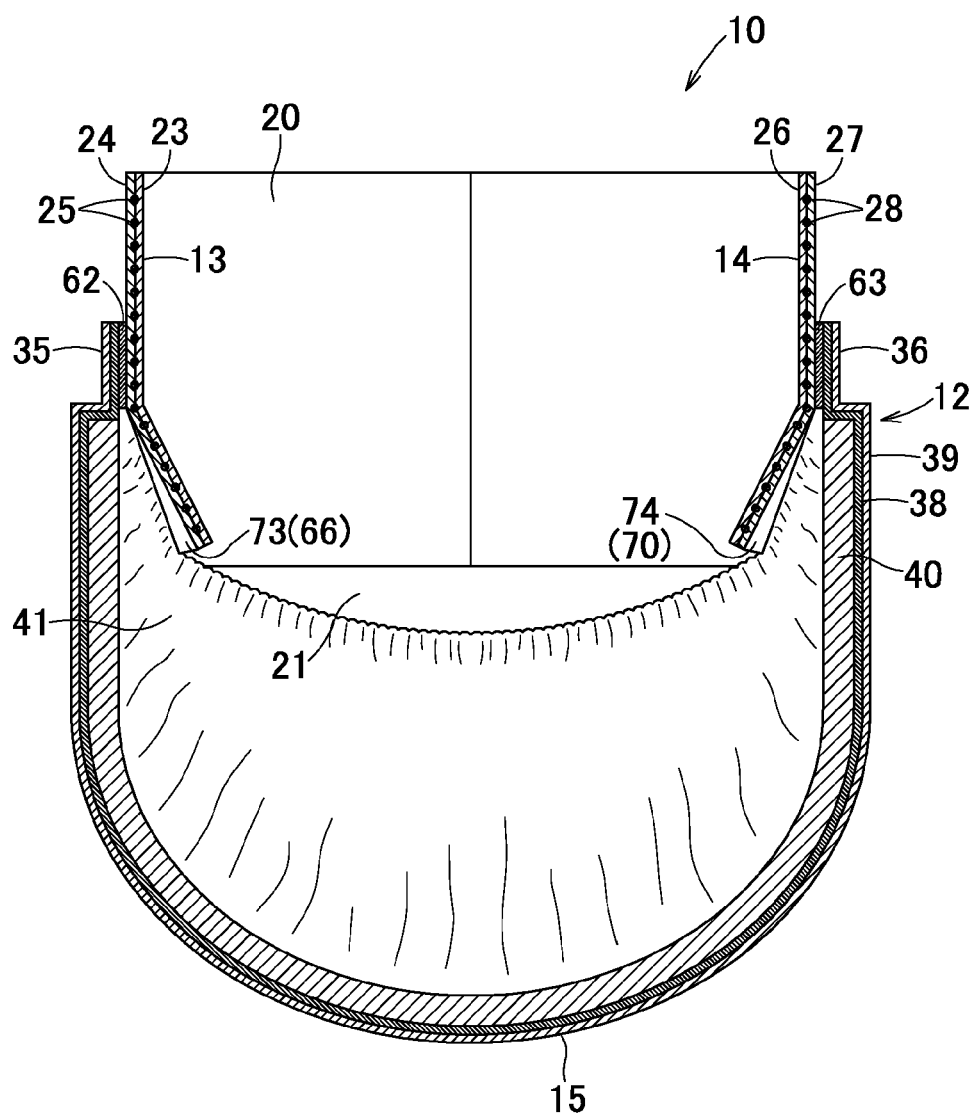
FIG. 5 is a schematic sectional view taken along line V-V in FIG. 1.
Figure 6:
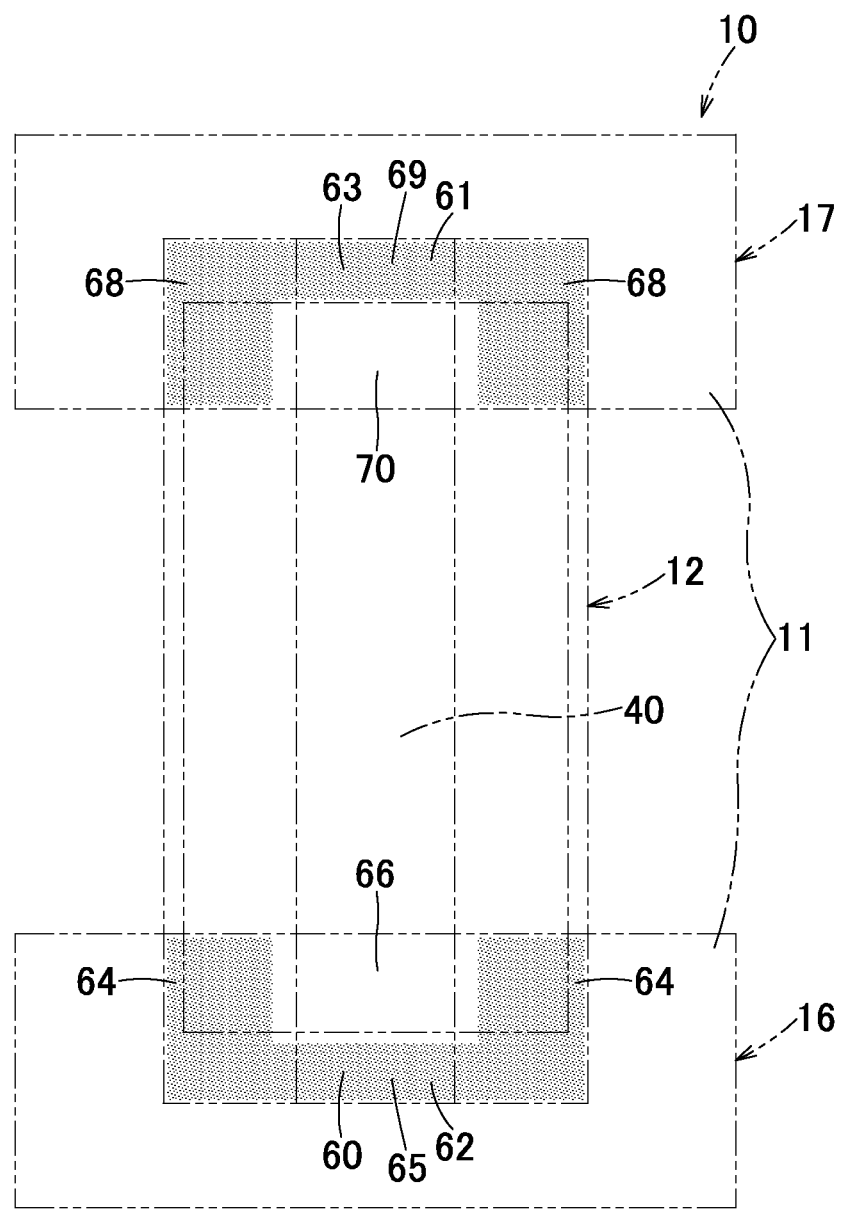
FIG. 6 is a developed plan view of the diaper, showing an arrangement of front and rear bonded regions.

FIG. 1 is a perspective view of a disposable diaper 10 as one example of the disposable wearing articles of the present invention, FIG. 2 is a partially cutaway developed plan view of the diaper 10 having front and rear waist regions peeled off from each other along side seams 18 and developed in a front-back direction as viewed from the inner side of the diaper, FIG. 3 is a sectional view taken along line III-III in FIG. 2, FIG. 4 is a sectional view taken along line IV-IV in FIG. 2, FIG. 5 is a schematic sectional view taken along line V-V in FIG. 1 and FIG. 6 is a developed plan view of the diaper, showing an arrangement of front and rear bonded regions 62, 67. In FIG. 6, elastic waist panels 16, 17 and a crotch member 12 are indicated by imaginary lines for convenience of illustration.

Referring to FIGS. 1 and 2, the disposable diaper 10 has a longitudinal direction Y and a transverse direction X orthogonal thereto, an imaginary center line P-P bisecting a width dimension of the diaper 10 in the transverse direction X, including a side facing the wearer's skin, a side facing away from the wearer's skin, an annular elastic waist panel 11, and a crotch member 12 attached to the side of the elastic waist panel 11 facing away from the wearer's skin so as to define a front waist region 13, a rear waist region 14 and a crotch region 15 extending between the front and rear waist regions 13, 14 in the longitudinal direction Y. The diaper 10 is symmetrically formed about the imaginary center line P-P. The elastic waist panel 11 includes a front waist panel 16 defining the front waist region 13 and a rear waist panel 17 defining the rear waist region 14.

The front waist panel 16 has a horizontally long and substantially rectangular shape contoured by an inner end 16a intersecting with the crotch member 12 and extending in the transverse direction X, an outer end 16b spaced from and opposed to the inner end 16a in the longitudinal direction Y and extending in the transverse direction X and opposite side edges 16c, 16d extending between the inner and outer ends 16a, 16b in the longitudinal direction Y.

The rear waist panel 17 is substantially the same as the front waist panel 16 in shape as well as in size and contoured by an inner end 17a intersecting with the crotch member 12 and extending in the transverse direction X, an outer end 17b spaced from and opposed to the inner end 17a in the longitudinal direction Y and extending in the transverse direction X and opposite side edges 17c, 17d extending between the inner and outer ends 17a, 17b in the longitudinal direction Y.

The opposite side edges 16c, 16d of the front waist panel 16 are respectively connected to the opposite side edges 17c, 17d of the rear waist panel 17 along the side seams 18 formed by sealing intermittently in the longitudinal direction Y whereupon a waist-opening 20 and a pair of leg-openings 21 are formed (See FIG. 1). The side seams 18 are formed by known sealing techniques such as hot embossing or ultrasonic sealing treatments.

The front waist panel 16 includes a first inner sheet 23 lying on the side facing the wearer's skin and a first outer sheet 24 lying on the side facing away from the wearer's skin. Both the first inner sheet 23 and the first outer sheet 24 may be formed for example, of a liquid-impervious SMS nonwoven fabric, a spun bonded nonwoven fabric, a plastic sheet or a laminated sheet thereof, each having a mass per unit area of 15 to 30 g/m². These two sheets 23, 24 may be bonded to each other with a hot melt adhesive (not shown) applied to inner surface of at least one of these sheets 23, 24. A plurality of strand-like or string-like front waist elastic elements 25 extending in the transverse direction X may be attached under tension and in a contractible manner with a hot melt adhesive (not shown) between the first inner sheet 23 and the first outer sheet 24 to elasticize the front waist panel 16 at least in the transverse direction X. It should be appreciated that the first inner sheet 23 and the first outer sheet 24 may be bonded to each other merely by the intermediary of a hot melt adhesive applied to the respective elastic elements used as the front waist elastic elements 25.

The rear waist panel 17 includes a second inner sheet 26 lying on the side facing the wearer's skin and a second outer sheet 27 lying on the side facing away from the wearer's skin. Both the second inner sheet 26 and the first outer sheet 27 may be formed for example, of a liquid-impervious SMS nonwoven fabric, a spun bonded nonwoven fabric, a plastic sheet or a laminated sheet thereof, each having a mass per unit area of 15 to 30 g/m². These two sheets 26, 27 may be bonded to each other with a hot melt adhesive (not shown) applied to inner surface of at least one of these sheets 26, 27. A plurality of strand-like or string-like front waist elastic elements 28 extending in the transverse direction X may be attached under tension and in a contractible manner with a hot melt adhesive (not shown) between the second inner sheet 26 and the second outer sheet 27 to elasticize the rear waist panel 17 at least in the transverse direction X. It should be appreciated that the second inner sheet 26 and the second outer sheet 27 may be bonded to each other merely by the intermediary of a hot melt adhesive applied to the respective elastic elements used as the front waist elastic elements 28.

The crotch member 12 is contoured by a front end 31 extending in the transverse direction X in the front waist region 13, a rear end 32 spaced from and opposed to the front end 31 in the longitudinal direction Y and extending in the transverse direction X and opposite side edges 33, 34 extending in the longitudinal direction Y so that the crotch member 12 has a substantially rectangular shape as viewed in the developed diaper 10 (See FIG. 2).

The crotch member 12 has a front end 35 attached to the outer surface of the front waist panel 16, a rear end 36 attached to the outer surface of the rear waist panel 17, an intermediate portion 37 extending in the longitudinal direction Y between the front and rear ends 35, 36, liquid-impervious crotch inner and outer sheets 38, 39 and a liquid-absorbent structure 40 laid on the side of the crotch inner sheet facing the wearer's skin. The crotch inner and outer sheets 38, 39 are bonded to each other with a hot melt adhesive (not shown) applied to the inner surface of at least one of the sheets 38, 39. Respective opposite side edges of these inner and outer sheets 38, 39 are folded inward to define a pair of lateral elastic regions 41 extending in the longitudinal direction Y on the inner surface of the liquid-absorbent structure 40. The liquid-absorbent structure 40 is formed from a semi-rigid absorbent core having stiffness higher than that of the inner and outer sheets and including at least a mixture of super-absorbent polymer particles and fluff pulp fibers wrapped with a liquid-pervious sheet.

The respective lateral elastic regions 41 have inner side edges 42 including respective opposite side edges of the crotch inner and outer sheets 38, 39 bonded together and front and rear ends 44, 45. In the course of making the diaper 10, the respective lateral elastic regions 41 are folded along respective fold lines (i.e., the opposite side edges 33, 34 of the crotch member 12) of the crotch inner and outer sheets 38, 39 to define outer side edges 43 extending in the longitudinal direction Y.

Along the front and rear ends 44, 45 of the respective lateral elastic regions 41, front and rear ends of the crotch inner sheet 38 forming the respective lateral elastic regions 41 are bonded to front and rear ends of the crotch outer sheet 39 by the intermediary of respective adhesive zones 48, 49 extending in the transverse direction X. By sealing the front and rear ends 44, 45 of the respective lateral elastic regions 41 in this manner, body waste having penetrated into the respective lateral elastic regions 41 through the front and rear ends 44, 45 would not leak out from the diaper 10. Though not illustrated, the front and rear ends 44, 45 of the respective lateral elastic regions 41 are secured to the crotch inner sheet 38 forming the front and rear ends 31, 32 of the crotch member 12 by various types of bonding means such as adhesives. Having the front and rear ends 44, 45 of the respective lateral elastic regions 41 secured to the front and rear ends 31, 32 of the crotch member 12, body waste excreted onto the liquid-absorbent structure 40 would not leak out from the diaper 10 through a gap which would otherwise be left between the front and rear ends 44, 45 of the respective lateral elastic regions 41 and the front and rear ends 31, 32 of the crotch member 12. It should be appreciated here that the adhesive zones 48, 49 may be formed by various types of adhesives such as a hot melt adhesive which is of the same type as or different from the hot melt adhesive applied to the respective entire inner surfaces of the crotch inner and outer sheets 38, 39 or the other sealing techniques such as heat sealing or ultrasonic sealing treatments or a combination thereof.

Referring to FIGS. 2 through 5, each of the lateral elastic regions 41 is provided with a first leg elastic member 50 and a second leg elastic member 51 respectively include two or more strand- or string-like elastic elements extending in the longitudinal direction Y to elasticize the associated lateral region 41 at least in the longitudinal direction Y. Specifically, the first leg elastic member 50 includes three (3) elastic elements extending in the longitudinal direction Y along the inner side edge of the associated lateral elastic region 41 and the second leg elastic member 51 include five (5) elastic elements concavely curved inward in a middle zone of the crotch region 15 and then rectilinearly extending toward the front and rear waist regions 13, 14. The first and second leg elastic members 50, 51 are interposed and secured between the crotch inner and outer sheets 38, 39 under tension in the longitudinal direction Y by the intermediary of a hot melt adhesive (not shown) applied to the inner surface of at least one of the crotch inner and outer sheets 38, 39.

As will be apparent from FIGS. 3 and 4, respective side edges of the crotch inner and outer sheets 38, 39 are exactly put flat and integrally bonded together along the inner side edges 42 of the respective lateral elastic regions 41. Specifically, the crotch inner and outer sheets 38, 39 are integrated by a hot melt adhesive applied planarly or in a fibrous form thereto to ensure a sealing effect for the interior spaces of the respective lateral elastic regions 41 and thereby to prevent the first leg member 50 from falling off through the respective inner side edges 42. Should the side edges of the crotch inner and outer sheets 38, 39 be bonded together in a state out of alignment along the respective inner edges of the lateral elastic regions 41, body waste might leak out of the diaper 10 through a gap left between the side edges of the crotch inner and outer sheets 38, 39. However, according to the present embodiment, the side edges of the crotch inner and outer sheets 38, 39 are put flat and integrally bonded together substantially in a well aligned state and such leakage should not occur.

With the diaper 10 put on the wearer's body, the lateral elastic regions 41 are spaced apart from the liquid-absorbent structure 40 and come in contact with the wearer's inguinal region since the first and second leg elastic members 50, 51 are secured to the lateral elastic regions 41. In consequence, the crotch member 12 has a form of bag slung own from the elastic waist panel 11 (See FIG. 1). When body waste is excreted onto the liquid-absorbent structure 40 of the diaper 10 put on the wearer's body in this manner, the liquid-absorbent structure 40 is spaced apart from the wearer's buttock under its own weight to form a space between the wearer's buttock and the liquid-absorbent structure 40. This space can serve as a body waste retaining space having a capacity larger than in the conventional disposable diaper.

Referring to FIGS. 2 through 6, the front end 35 and the rear end 36 of the crotch member 12 are coated on the side thereof facing the wearer's skin with hot melt adhesives 60, 61 to form a front bonded region 62 and a rear bonded region 63 in which the crotch member 12 is attached to the outer surface of the front and rear waist panels 16, 17. By attaching the front end 35 and the rear end 36 to the outer surface of the front and rear waist panels 16, 17 in this manner, it is possible to form the large volumetric body waste retaining space. It should be appreciated that only one of the front end 35 and the rear end 36 may be attached to the outer surface of the associated waist panel 16 or 17 so long as the retaining space for body waste can be effectively enlarged. If the rear end 36 is attached to the outer surface of the rear waist panel 17, the body waste retaining space having a shape well conforming to the shape of the wearer can be obtained and thereby wearing feeling the diaper 10 can be improved.

The front bonded region 62 opens toward the crotch region 15 in a concave shape, i.e., a so-called square U-shape and includes opposite lateral zones 64 defined by the front ends of the respective lateral elastic regions 41 coated with a hot melt adhesive and an intermediate zone 65 extending from the respective lateral zones 64. Inner side edges of the respective lateral zones 64 lie slightly inner than the respective inner side edges 42 of the respective lateral elastic regions 41 and the intermediate zone 65 lie outer than the region occupied by the liquid-absorbent structure 40. A front non-bonded region 66 coated with no hot melt adhesive 60 is defined between the lateral zones 64 and the intermediate zone 65.

Likewise, the rear bonded region 63 opens toward the crotch region 15 in a concave shape, i.e., a so-called square U-shape and includes opposite lateral zones 68 defined by the rear ends of the respective lateral elastic regions 41 coated with a hot melt adhesive and an intermediate zone 69 extending between the respective lateral zones 68 in the transverse direction X. Inner side edges of the respective lateral zones 68 lie slightly inner than the respective inner side edges 42 of the respective lateral elastic regions 41 and the intermediate zone 69 lie outer than the region occupied by the liquid-absorbent structure 40 as viewed in the longitudinal direction X. A rear non-bonded region 70 coated with no hot melt adhesive 60 is defined between the lateral zones 68 and the intermediate zone 69.

As illustrated in FIG. 5, the non-bonded regions 66, 70 defined in the front and rear ends 35, 36 of the crotch member 12 allow spaces to be defined between the crotch member 12 and the front and rear waist panels 16, 17, respectively. These spaces function as body waste retaining spaces 73, 74. Within these body waste retaining spaces 73, 74, the front and rear ends of the liquid-absorbent structure 40 are respectively present and rapidly absorb urine flowing into the respective body waste retaining spaces 73, 74.

While both the front bonded region 62 and the rear bonded region 63 have the square U-shapes respectively defining the non-bonded regions 66, 70 according to the present embodiment, an alternative arrangement is also possible in which only one of the non-bonded regions 66, 70 has the square U-shape and the other non-bonded region has no body waste retaining space formed by the non-bonded region. Also, regarding the front and rear bonded regions 62, 63, the other alternatives are possible as long as the body waste retaining space or spaces is or are defined. Specifically, the inner side edges thereof or these bonded regions as a whole may have a curved shape; the lateral zones 64, 68 and/or the intermediate zones 65, 69 may have a stepped shape; and the lateral zones 64, 68 may have a triangular shape.

Second Embodiment

FIG. 7 is a plan view similar to FIG. 6, showing a second embodiment of the present invention. It should be appreciated that the respective components (except the front and rear bonded regions 62, 63) of the waist panel 11 and the crotch member 12 of the diaper 10 are indicated by imaginary lines in FIG. 7 for convenience of illustration. The basic construction of the diaper 10 according to the present embodiment is similar to that of the first embodiment and therefore the following description will be limited to the features different from those of the first embodiment.

According to the present embodiment, leakage-barrier sheets 75, 76 made of liquid-impervious plastic sheets or fibrous nonwoven fabric sheets each having slightly larger areas than those of the respective non-bonded regions 66, 70 are provided in the respective front and rear non-bonded regions 66, 70.

More specifically, the respective leakage-barrier sheets 75, 76 are interposed and secured with a hot melt adhesive (not shown) between the first inner sheet 23 and the first outer sheet 24 forming together the front waist panel 16 and between the second inner sheet 26 and the second outer sheet 27 forming together the rear waist panel 17. The leakage-barrier sheets 75, 76 provided in the areas of the front and rear non-bonded regions 66, 70 in this manner can reliably prevent urine from leaking out beyond the front and rear waist panels 16, 17 even if urine having flowed into the waste retaining spaces 73, 74 is not completely absorbed by the liquid-absorbent structure 40 and leaches out from the crotch member 12. While the leakage-barrier sheets 75, 76 are interposed between the first inner and outer sheets 23, 24 and between the second inner and outer sheets 26, 27, respectively, according to the present embodiment, it is possible to attach these leakage-barrier sheets 75, 76 to the respective inner surfaces of the first and second inner sheets 23, 26 with a hot melt adhesive.

As materials for the respective component members or elements of the elastic waist panel 11 and the crotch member 12 are not limited to those which have been described with respect to the first and second embodiments of the present invention and the other various materials widely used in the related technical field may be selectively used without departing from the scope of the present invention. While the diaper 10 having been described above as the embodiments of the present invention is a so-called pants-type diaper in which the elastic waist panel 11 and the crotch member 12 are separately formed, the present invention may be implemented in the form of a diaper in which a liquid-absorbent core is interposed between a pair of generally hourglass-shaped sheets and also in the form of a so-called open-type diaper.

REFERENCE SIGNS LIST 10 disposable diaper
11 elastic waist panel
12 crotch member
13 front waist region
14 rear waist region
15 crotch region
35 front end of crotch member
36 rear end of crotch member
40 liquid-absorbent structure
41 elastic lateral region
62 front bonded region
63 rear bonded region
66, 70 non-bonded regions
73, 74 body waste retaining spaces
75, 76 leakage-barrier sheets
X transverse direction
Y longitudinal direction

The invention claimed is:

1. A disposable wearing article having a longitudinal direction and a transverse direction orthogonal thereto, a skin facing side for facing a wearer when the wearing article is worn and a non-skin facing side opposite to the skin facing side in a thickness direction of the wearing article, the wearing article comprising:
a front waist region;
a rear waist region;
a crotch region extending between the front and rear waist region;
an annular elastic waist panel including a front waist panel defining the front waist region and a rear waist panel defining the rear waist region; and
a crotch member attached to the elastic waist panel so as to define and defining parts of the front and rear waist regions and the crotch region,
wherein the crotch member has a front end lying in the front waist region and a rear end lying in the rear waist region,
at least one of the front and rear waist panels includes:
a non-bonded region in an intermediate zone of the front and/or rear waist panel as viewed in the transverse direction; and
a bonded region where an outer surface of the front and/or rear waist panel is attached to an inner surface of the front and/or rear end of the crotch member, by the intermediary of a square U-shaped bonded region opening toward the crotch region,
the non-bonded region between the front and/or rear waist panels and the front and/or rear end of the crotch member define a body waste retaining space for protecting the wearer's skin from being soiled with bodily waste.

2. The wearing article defined by claim 1, wherein
the crotch member comprises
a pair of lateral elastic regions extending in the longitudinal direction on opposite sides of the crotch region; and
a liquid-absorbent structure extending in the longitudinal direction on an inner surface of the crotch region, and
the non-bonded region is defined in an area occupied by the liquid-absorbent structure between the pair of lateral elastic regions.

3. The wearing article defined by claim 1, further comprising:
liquid-impervious leakage-barrier sheets including a moisture-pervious plastic sheet or a fibrous nonwoven fabric sheet,
wherein the leakage-barrier sheets are attached to the elastic waist panel in regions corresponding to the non-bonded regions.

4. The wearing article defined by claim 1, wherein the crotch member further comprises liquid-impervious crotch inner and outer sheets, and a liquid-absorbent structure laid on the crotch inner sheet and on the skin facing side.

5. The wearing article defined by claim 4, wherein the crotch inner and outer sheets are joined to each other by adhesive without sandwiching the liquid-absorbent structure in the thickness direction.

6. The wearing article defined by claim 5, wherein the adhesive is applied to an inner surface of at least one of the crotch inner and outer sheets.

7. The wearing article defined by claim 5, wherein the crotch inner and outer sheets comprise opposite side edges folded inward to define a pair of lateral elastic regions extending in the longitudinal direction on an inner surface of the liquid-absorbent structure.

8. The wearing article defined by claim 7, wherein
the pair of lateral elastic regions comprises front and rear ends in the front and rear waist regions correspondingly, and
front and rear ends of the crotch inner sheet are bonded to front and rear ends of the crotch outer sheet along the front and rear ends of the pair of lateral elastic regions and by adhesive extending in the transverse direction.

9. The wearing article defined by claim 1, wherein the crotch member has a liquid-absorbent structure in the crotch region, and the body waste retaining space is provided between the liquid-absorbent structure and the elastic waist panel.

* * * * *